(12) United States Patent
Uihlein

(10) Patent No.: US 11,185,316 B2
(45) Date of Patent: Nov. 30, 2021

(54) MEDICAL NET-AND-LOOP TYPE RETRIEVAL INSTRUMENT

(71) Applicant: EPflex Feinwerktechnik GmbH, Dettingen/Erms (DE)

(72) Inventor: Bernhard Uihlein, Dettingen (DE)

(73) Assignee: EPflex Feinwerktechnik GmbH, Dettingen/Erms (DE)

( * ) Notice: Subject to any disclaimer, the term of this patent is extended or adjusted under 35 U.S.C. 154(b) by 300 days.

(21) Appl. No.: 16/474,951

(22) PCT Filed: Dec. 21, 2017

(86) PCT No.: PCT/EP2017/084275
§ 371 (c)(1),
(2) Date: Jun. 28, 2019

(87) PCT Pub. No.: WO2018/122136
PCT Pub. Date: Jul. 5, 2018

(65) Prior Publication Data
US 2019/0343501 A1    Nov. 14, 2019

(30) Foreign Application Priority Data
Dec. 29, 2016  (DE) .................... 10 2016 226 295.5

(51) Int. Cl.
*A61B 17/00* (2006.01)
*A61B 17/221* (2006.01)
(52) U.S. Cl.
CPC .............. *A61B 17/00234* (2013.01); *A61B 2017/00287* (2013.01); *A61B 2017/00358* (2013.01); *A61B 2017/2212* (2013.01)

(58) Field of Classification Search
CPC ............ A61B 17/00234; A61B 17/221; A61B 17/3423; A61B 2017/00287; A61B 2017/00358; A61B 2017/2212
See application file for complete search history.

(56) References Cited

U.S. PATENT DOCUMENTS

| 5,486,182 | A | 1/1996 | Nakao et al. |
| 5,735,289 | A | 4/1998 | Pfeffer et al. |
| 6,696,120 | B1* | 2/2004 | Todt .................... B65D 81/03 206/497 |
| 2004/0255739 | A1 | 12/2004 | Clifford et al. |

(Continued)

FOREIGN PATENT DOCUMENTS

| EP | 0 583 964 B1 | 7/1998 |
| EP | 1 967 146 A2 | 9/2008 |

(Continued)

OTHER PUBLICATIONS

International Search Report (PCT/ISA/210) issued in PCT Application No. PCT/EP2017/084275 dated Apr. 18, 2018 with English translation (seven (7) pages).

(Continued)

*Primary Examiner* — Mohamed G Gabr
(74) *Attorney, Agent, or Firm* — Crowell & Moring LLP

(57) ABSTRACT

A medical net-and-loop type retrieval instrument has a distal loop and a retrieval net held on the loop by way of a net holding portion that is firmly held in the interior of the cross section of the loop. The medical net-and-loop type retrieval instrument is suitable for use in medical endoscopy.

13 Claims, 7 Drawing Sheets

(56) References Cited

U.S. PATENT DOCUMENTS

2009/0192510 A1* 7/2009 Bahney ............... A61B 17/221
                                                                606/45
2016/0081702 A1  3/2016 Kan et al.

FOREIGN PATENT DOCUMENTS

EP         2 085 045 A1    8/2009
WO    WO 2008/154406 A1   12/2008

OTHER PUBLICATIONS

German-language Written Opinion (PCT/ISA/237) issued in PCT Application No. PCT/EP2017/084275 dated Apr. 18, 2018 (six (6) pages).
German-language Office Action issued in counterpart German Application No. 10 2016 226 295.5 dated Oct. 16, 2017 (six (6) pages).

* cited by examiner

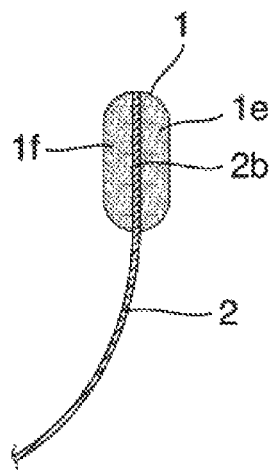
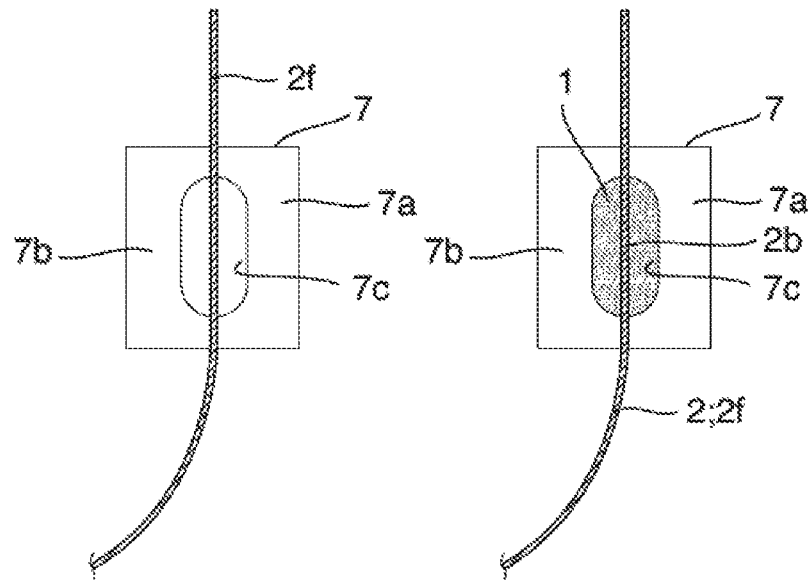
Fig. 17  Fig. 18  Fig. 19
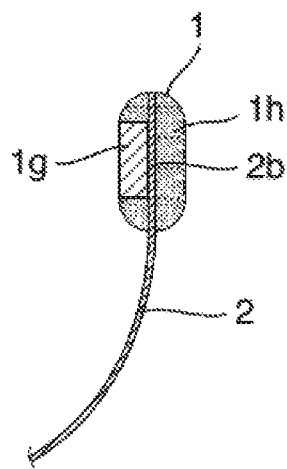
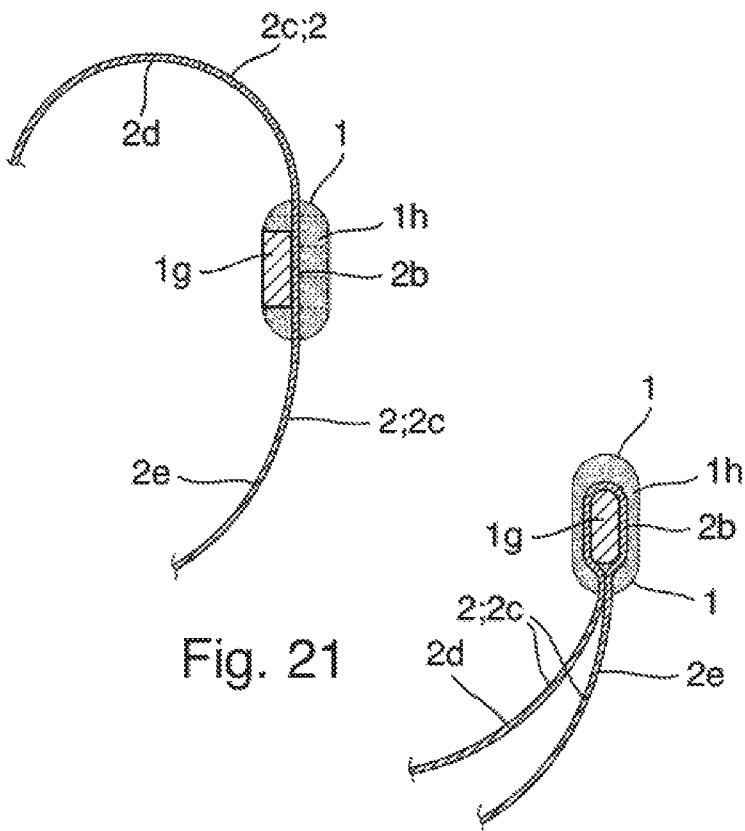
Fig. 20  Fig. 21  Fig. 22

MEDICAL NET-AND-LOOP TYPE RETRIEVAL INSTRUMENT

CROSS REFERENCE TO RELATED APPLICATIONS

This application is a national phase entry of PCT International Application No. PCT/EP2017/084275, filed Dec. 21, 2017, which claims priority under 35 U.S.C. § 119 from German Patent Application No. 10 2016 226 295.5, filed Dec. 29, 2016, the entire disclosures of which are herein expressly incorporated by reference.

BACKGROUND AND SUMMARY OF THE INVENTION

The invention relates to a medical net-and-loop type retrieval instrument comprising a distal loop and a retrieval net that by way of a net holding portion is held on the loop. Instruments of this type are in particular used in the medical endoscopy technology, for example as a polypectomy loop instrument in endoscopic polypectomy.

In the case of instruments of this type, it is known for the retrieval net to be quasi threaded onto the distal loop, that is to say that respective portions of the woven net fabric are loosely wound about the loop. In order for displacement movements of the retrieval net along the loop to be minimized, holding snares of an additional holding thread can be provided, said holding snares enclosing the loop and an adjacent piece of the woven fabric of the retrieval net at the respective connection location. The first and unexamined publication WO 2008/154406 A1 discloses such a conventional net-and-loop type instrument.

A further conventional net-and-loop type retrieval instrument of this type for enclosing a shaped internal organ or tissue during endoscopic surgery in a bio-absorbable surgical pouch is disclosed in the patent document EP 0 583 964 B1. The retrieval net therein is formed by the pouch which on the circumferential periphery thereof has a seam through which the loop is threaded.

The conventional net-and-loop type retrieval instruments mentioned above in terms of the production thereof are relatively complex, and undesirable displacements of the retrieval net along the loop can arise when in use.

It is an object of the invention to provide a net-and-loop type retrieval instrument of the type mentioned at the outset which avoids or in any case reduces the above-mentioned difficulties of the prior art and which can in particular be produced by way of a relative minor complexity and in which the retrieval net can be held on the loop in a comparatively secure manner such that no undesirable displacements of the retrieval net along the loop arise.

The invention achieves this and other objects by providing a net-and-loop type retrieval instrument comprising a distal loop and a retrieval net that by way of a net holding portion is held on the loop, wherein the retrieval net by way of the net holding portion is firmly held by the loop in the interior of the cross section of the loop.

In the case of the net-and-loop type retrieval instrument, the retrieval net by way of the net holding portion thereof is held by the loop in the interior of the cross section of the loop. On account thereof, any displacement of the retrieval net along the loop can be readily avoided, and this mounting of the retrieval net on the loop can be implemented by way of a relatively minor complexity in terms of production technology. Additional holding snares for linking the retrieval net to the loop and/or for avoiding undesirable displacement movements of the retrieval net along the loop are not required. The loop, on the surface thereof and in particular on the radially outer periphery thereof and/or on the radially inner periphery thereof can be held so as to be entirely free or at least largely free of the retrieval net and consequently there have a smooth profile without said smooth profile being disturbed by retrieval net parts or holding parts such as holding snares and the like that are situated there.

In a refinement of the invention, the loop comprises at least two conforming loop parts, that is to say that the loop parts have a congruent loop shape. The conforming loop parts bear on one another and in this mutually bearing position are connected to one another so as to form the loop, wherein said conforming loop parts therebetween leave a net receptacle gap. The retrieval net by way of the net holding portion thereof is firmly held in said net receptacle gap. The loop parts can be separately prefabricated, for example, and then be fastened to one another. Identical or different materials can be used for the loop parts, for example all materials being from metal or all materials being from plastics material, or at least one material being from metal and at least one other material being from plastics material. Arbitrary materials which are known per se for this purpose, including super elastic materials, can presently be used as metal or plastics materials, respectively, for the loop.

In one design embodiment of the invention, at least a first and a second of the loop parts are fixed to one another by means of at least one clamped joint connection and/or one adhesively bonded joint connection and/or at least one welded/soldered joint connection. Depending on the requirement and the specific application, this advantageously represents implementable connections of the loop parts in order for the latter to be mutually fixed. The retrieval net can optionally also be included in the mutual fixing of the loop parts, said retrieval net in this case between at least two of the loop parts being fixedly clamped/jammed and/or being adhesively bonded and/or welded/soldered to at least one of the loop parts and thus being firmly held in the net receptacle gap. Alternatively, the retrieval net is firmly held in the net receptacle gap by way of a connection that is independent of the mutual fixing of the loop parts.

In one design embodiment of the invention, the mutual fixing of at least the first and second loop part includes the use of a clip which encompasses at least said two loop parts in a conjointly clamping manner, either along the entire length of the loop or at least in portions on one or a plurality of locations spaced apart along the loop. This type of fixing can have advantages in terms of production technology and optionally simultaneously serve for holding the retrieval net so as to be firmly clamped in the net receptacle gap.

In one design embodiment of the invention, the loop comprises an outer and an inner loop part, wherein the outer loop part surrounds the inner loop part and by way of an internal circumference faces an external circumference of the inner loop part. In other words, the inner loop part has a somewhat smaller diameter, or a somewhat smaller loop width, respectively, than the outer loop part and is coaxially surrounded by said outer loop part. The inner and the outer loop part thus lie so as to be coaxial in the same loop plane. The net receptacle gap can be formed therebetween, the retrieval net for example being inserted or guided through, respectively in the axial direction, that is to say so as to be perpendicular to the loop plane, in said net receptacle gap.

In a refinement of the invention, which is an alternative to a multi-part embodiment, the loop is made integrally while embedding the net holding portion of the retrieval net in the interior of the cross section of the loop. To this end, the loop can be made as a cast component from metal and/or plastics material, the retrieval net by way of the net holding portion being cast therein, in particular as a single-component plastics material injection molded part or in one design embodiment of the invention as a multi-component plastics material injection molded part having at least one first loop component from metal or plastics material, and a second loop component molded thereon, preferably from plastics material, wherein the retrieval net by way of the net holding portion thereof is held so as to be cast between the loop components. This implementation of the net-and-loop retrieval instrument according to the invention also guarantees a secure mounting of the retrieval net in combination with a functionally advantageous design of the loop at a relatively minor production complexity.

In one refinement of the invention, the retrieval net is held on the loop by means of at least one clamped joint connection and/or at least one adhesively bonded connection and/or at least one welded/soldered joint connection. These represent advantageous types of connections between the loop and the retrieval net, wherein said retrieval net in the case of a loop constructed from multiple parts can be connected to only one part, a plurality of parts, or all parts of the loop, depending on the requirement and on the specific application.

In one refinement of the invention, the retrieval net is formed by a woven-fabric net pouch which, by way of the pouch periphery, is firmly held on the loop, that is to say that the pouch periphery in this case forms the net holding portion of the retrieval net. This embodiment of the retrieval net is advantageous for corresponding applications, and the fastening of the retrieval net to the loop is performed in a simple manner by firmly holding the pouch periphery in the interior of the loop cross section.

In an alternative refinement of the invention, the retrieval net is formed by a folded-together woven-fabric net hose piece which is circumferentially closed and which, in the circumferential direction, extends through the interior of the cross section of the loop. The retrieval net in this case is consequently embodied so as to be double-walled on account of the woven-fabric net hose piece being folded together. In the case of a loop constructed in multiple parts, a first of the loop parts can be placed into the woven-fabric net hose piece, and a second of the loop parts can be placed externally about the open-fabric net hose piece. In the case of an integral loop, the woven-fabric net hose piece by way of the circumferential part-portion as the net holding portion can be embedded in the cross section of the loop. The use of the woven-fabric net hose piece for forming the retrieval net enables an advantageously simple fixing of the retrieval net to the loop, in that said retrieval net in regions is cast in the loop, or in that at least the first loop part is placed in the interior of the hose piece and at least the second loop part is placed externally about the hose piece, respectively. Since the hose piece is circumferentially closed, no free woven-fabric ends which would have to be held on the loop are present on the circumference of the retrieval net. Rather, the retrieval net as a folded-together hose piece extends simply through the cross section of the loop and is held or fixed, respectively, in this position by the loop. This variant of embodiment can thus provide the retrieval net in the form of a woven fabric that is closed in an encircling manner without any free circumferential woven-fabric ends; free woven-fabric ends are at best present on the end side when the hose piece at the end side is not closed but open.

In one design embodiment of the invention, at least a first one of the loop parts by means of an adhesively bonded joint connection is connected to the net holding portion of the retrieval net and/or to at least a second one of the loop parts, said adhesively bonded joint connection being situated exclusively on an upper side of the loop, wherein the retrieval net extends into the loop only on an opposite lower side. This represents an implementation of the net-and-loop type retrieval instrument that is advantageous in terms of production technology and functionality. The adhesively bonded joint connection can be attached continuously or only in portions along the entire loop.

Advantageous embodiments of the invention are illustrated in the drawings and will be described hereunder. In the drawings herein:

BRIEF DESCRIPTION OF THE DRAWINGS

FIG. 17 shows the sectional view of FIG. 5 for a variant of an embodiment of the present invention having a single-component integral loop construction;

FIG. 18 shows a view for visualizing a step of a method in accordance with the present invention for producing the instrument of FIG. 17;

FIG. 19 shows the view of FIG. 18 for visualizing a further step of said method;

FIG. 20 shows the sectional view of FIG. 5 for a variant of an embodiment of the present invention having a dual-component integral loop construction;

FIG. 21 shows a sectional view of FIG. 20 for a variant of an embodiment of the present invention having a woven-fabric hose piece for the retrieval net;

FIG. 22 shows the sectional view of FIG. 20 for a further variant of an embodiment of the present invention having a woven-fabric hose piece for the retrieval net;

DETAILED DESCRIPTION OF THE DRAWINGS

Figure 1:
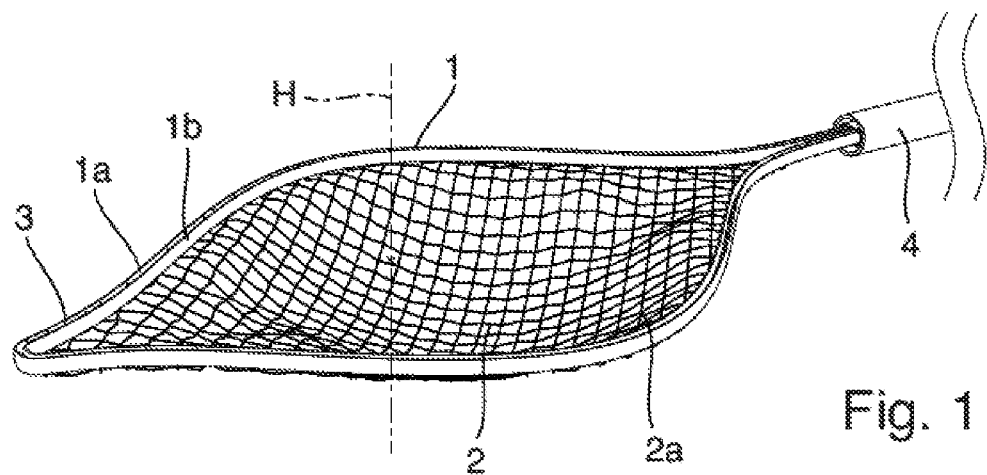
FIG. 1 shows a perspective view of a distal end region of the medical net-and-loop type retrieval instrument in accordance with an embodiment of the present invention having a loop from loop parts that lie radially beside one another and having a pouch-type retrieval net.
Figure 2:
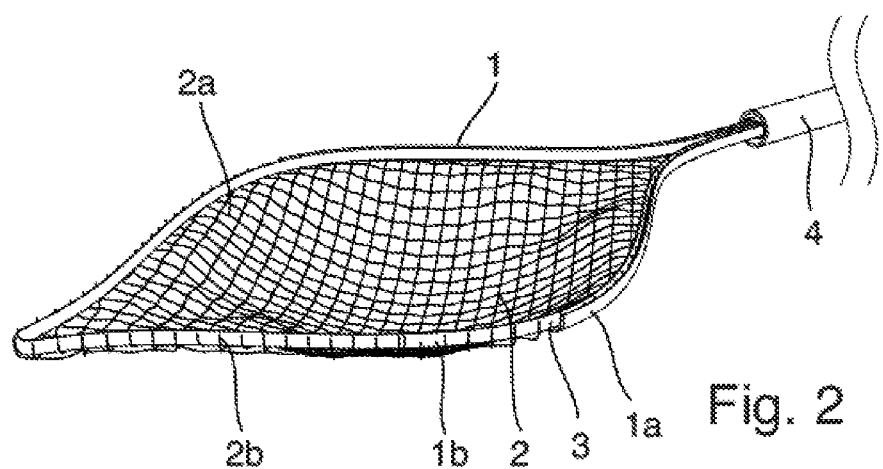
FIG. 2 shows the view of FIG. 1 having a partially cut-away external loop part.

FIGS. 1 to 24 show illustrations of embodiments of the medical net-and-loop type retrieval instrument according to the invention in the distal region thereof that is of interest here. The instrument has a distal loop 1 and a retrieval net 2 that is held on the loop 1. In the case of the embodiment of FIGS. 1 to 5, the loop 1 includes at least two conforming loop parts, that is to say two, three, four or more conforming loop parts, wherein said loop 1 in the case shown includes two loop parts in the form of a first outer loop part 1a and of a second inner loop part 1b. The at least two conforming loop parts 1a, 1b, while therebetween leaving a net receptacle gap 3, are connected so as to bear on one another, here specifically so as to lie in a radially juxtaposed manner. The retrieval net 2 by way of a net holding portion 2b is firmly held in the net receptacle gap 3 and is in this way, by way of the net holding portion 2b, firmly held by the loop 1 in the interior of the cross section of the loop 1, that is to say that the part of the retrieval net that is situated in the net receptacle gap 3 forms the net holding portion 2b. The loop parts 1a, 1b can in each case possess, for example, an elongated oval or a substantially rectangular cross section, as can be seen in FIGS. 1 to 5; the cross section of the loop 1 is accordingly composed of the cross sections of the loop parts 1a, 1b, having the net receptacle gap 3 therebetween.

The instruments shown can be used, for example, as a polypectomy loop instrument in the endoscopic polypectomy technique. To this end, the distal loop 1 in a manner known per se is retractable into a shaft-forming tube 4, or a shaft hose of the instrument, respectively, wherein the loop 1 is correspondingly contracted or folded together, respectively. To this end, the loop 1, likewise in a manner known per se and therefore not to be shown and explained in further detail here, is formed by a loop wire from metal or plastics material that is guided so as to be axially movable through the shaft tube 4. The loop wire and the tube 4 at a proximal end region of the instrument are coupled to an operating unit by way of which the user can move the loop wire axially relative to the tube 4. In this way, the user can move the loop 1, which in the initial state is completely received or retracted, respectively, into the tube 4, out of the tube 4, on account of which the loop 1 opens out from the folded-together state of said loop 1 in the tube 4 to the unfolded state of said loop 1, shown in FIGS. 1 to 4. Moving the loop 1 out of the tube 4 can be performed by sliding the loop wire forward and/or by moving the tube 4 backward. The loop wire can be composed of a super elastic or flexible metal or plastics material, for example, as is known per se. The two loop parts 1a, 1b herein, depending on the requirement, can be composed of the same material or of different materials, the latter potentially being two different plastics materials or two different metal materials, or the one part being composed of a plastics material and the other from a metal material.

The first and the second loop part 1a, 1b are preferably fixed to one another by means of at least one clamped joint connection and/or at least one adhesively bonded joint connection and/or at least one welded/soldered joint connection. This can be implemented, for example, by way of a plurality of adhesively bonded and/or welded/soldered joint connections which are provided so as to be mutually spaced apart along the loop 1.

Figure 3:
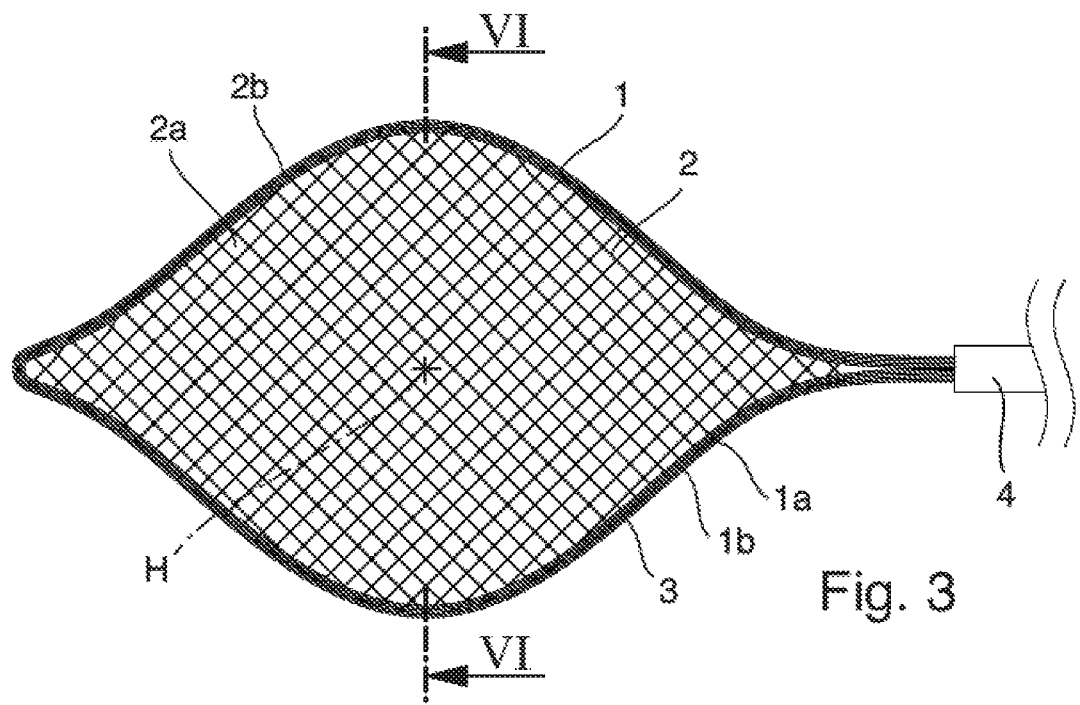
FIG. 3 shows a plan view of the distal instrument region of FIG. 1.
Figure 4:
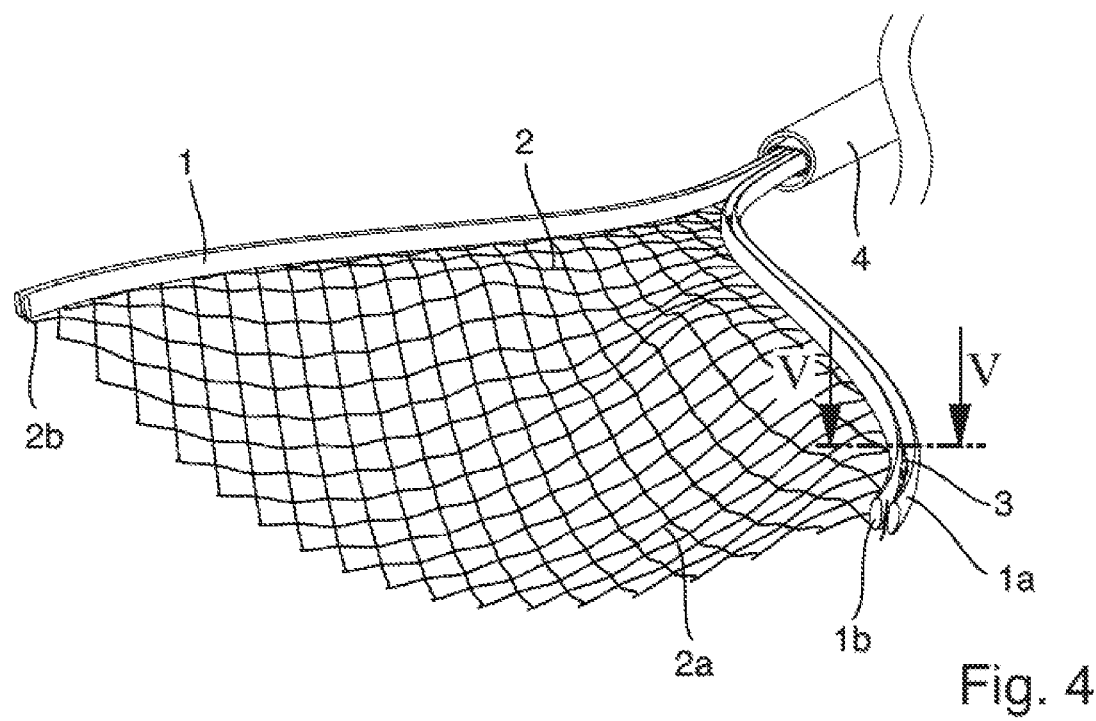
FIG. 4 shows a perspective view corresponding to that of FIG. 1, having a cut-away front half of the loop/retrieval net.
Figure 5:
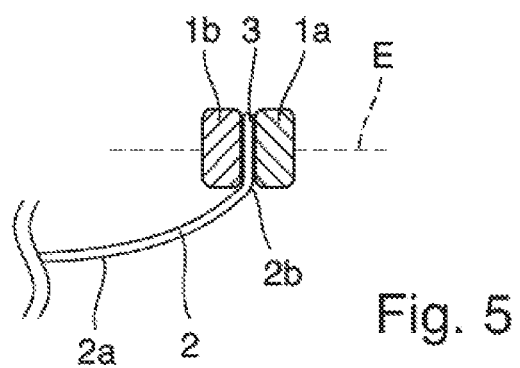
FIG. 5 shows a schematic sectional view along a line V-V in FIG. 4.

As can be seen from FIGS. 1 to 5, the outer loop part 1a surrounds the inner loop part 1b in a conforming manner, that is to say by way of an identical shape, and by way of an internal circumference faces an external circumference of the inner loop part 1b. To this end, the inner loop part 1b has a somewhat smaller diameter, or a somewhat smaller loop width, respectively, than the outer loop part 1a and is coaxially surrounded by the outer loop part 1a. The inner and the outer loop part 1b, 1a thus are coaxial in relation to a loop vertical axis H which is defined as a plane normal direction of a loop plane E that is spanned or defined by the loop 1 and in the plan view of FIG. 3 is thus perpendicular to the drawing plane. The retrieval net 2 in the view of FIG. 5 is inserted into the net receptacle gap 3 from below so as to be perpendicular to the loop plane E and thus so as to be axial, that is to say in the direction of the loop vertical axis H.

As is shown in the embodiment of FIGS. 1 to 5, the retrieval net 2 can be formed by a woven-fabric net pouch 2a which, by way of a pouch periphery as the net holding portion 2b, is firmly held in the net receptacle gap 3. To this end, it can, in particular, be provided for the retrieval net 2 by way of the pouch periphery thereof to be held on the loop 1 by means of at least one clamped joint connection and/or at least one adhesively bonded joint connection and/or at least one welded/soldered joint connection. For example, the retrieval net 2 by way of the pouch periphery thereof can be held so as to be firmly clamped along the entire length of the loop 1, or of the net receptacle gap 3, or at least on a plurality of clamping locations spaced apart along the loop 1, respectively. The clamping mechanism can be implemented in such a manner that the retrieval net 2 is securely held on the loop 1 solely on account of said clamping mechanism. Alternatively, the retrieval let 2 by way of the pouch periphery thereof can additionally be fixed to the inner or to the outer or to both loop parts 1b, 1a by one or a plurality of adhesively bonded joints and/or one or a plurality of welded joints/soldered joints. Free ends of the woven fabric used for the retrieval net 2 that are present on the pouch periphery can be received in the net receptacle gap 3 so that said free ends are not exposed or otherwise have to be reworked so as to form a seam, for example. The woven-fabric net of the retrieval net 2 can be composed of any suitable plastics material or metal material, in particular a material that is known per se for retrieval nets of polypectomy loop instruments.

Figure 6:
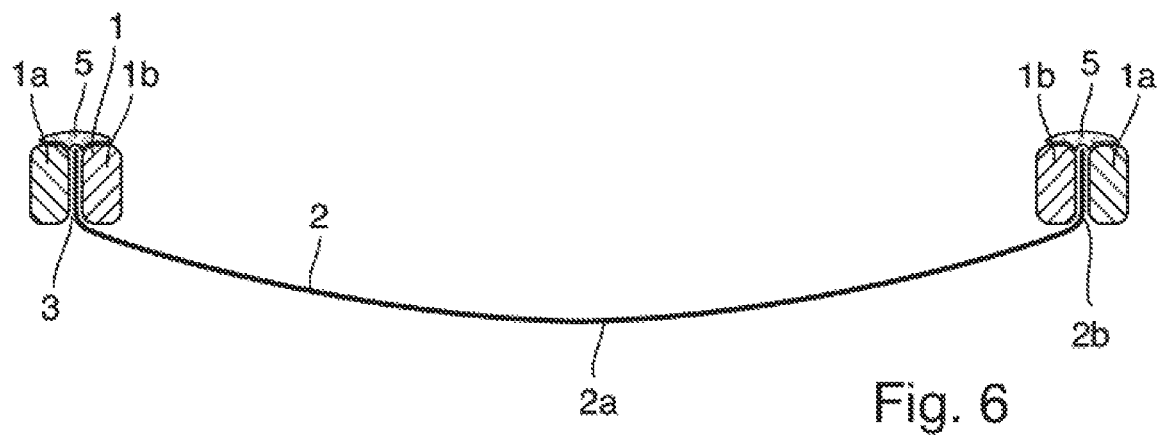
FIG. 6 shows a schematic sectional view along a line VI-VI in FIG. 3, for a variant having an additional adhesive connection.

FIG. 6 visualizes a variant of the embodiment shown in FIGS. 1 to 5, wherein as a single point of differentiation an adhesive material for forming one or a plurality of adhesively bonded joint connections 5 is applied to the upper side of the loop 1 in FIG. 6. This here can be a continuous adhesively bonded joint connection along the loop 1, or a plurality of adhesively bonded joint connections which are applied so as to be mutually spaced apart along the loop 1. Depending on the material of the two loop parts 1*a*, 1*b* and of the retrieval net 2, the adhesively bonded joint connection 5 establishes a fixing connection between the retrieval net 2, on the one hand, and the first loop part 1*a* and/or the second loop part 1*b*, on the other hand, or only between the two loop parts 1*a*, 1*b*. When the adhesively bonded joint connection 5 fixes the two loop parts 1*a*, 1*b* to one another, any other mutual fixing of the two loop parts 1*a*, 1*b* can optionally be dispensed with.

Figure 7:
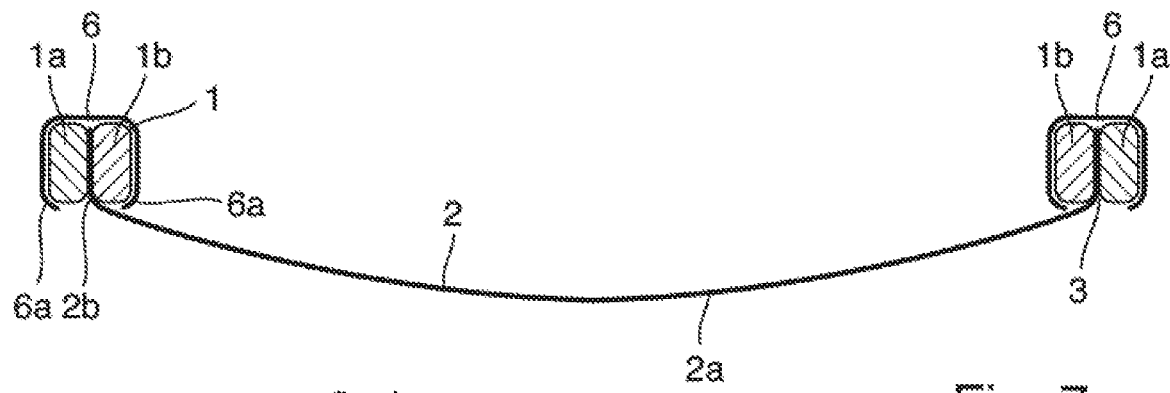
FIG. 7 shows the sectional view of FIG. 6 for a variant of an embodiment of the present invention having an additional clip.

FIG. 7 shows a further variant of an embodiment of the instrument of FIGS. 1 to 5, wherein this variant differs in that a clip 6 which at least in portions encompasses the loop parts 1*a*, 1*b* as to conjointly clamp the latter is additionally provided. Depending on the requirement and the specific application, the clip 6 can extend continuously along the length of the loop 1 or include one or a plurality of individual clip parts which are plug-fitted so as to be mutually spaced apart at different locations along the length of the loop 1. The clip in the example shown in FIG. 7 possesses a substantially U-shaped cross section having slightly inward-pointing free clip ends 6*a*. The clip 6 in FIG. 7 is placed from above onto the loop 1 and by way of the inward-facing free clip ends 6*a* of said clip 6 engages behind the loop 1, or the two loop parts 1*a*, 1*b* of said loop 1, respectively. The clip 6 leaves the net receptacle gap 3 free on that side, the lower side in FIG. 7, on which the retrieval net 2 by way of the pouch periphery thereof, or the net holding portion 2*b*, respectively, is inserted in the net receptacle gap 3.

The clip 6 ensures secure clamping and thus reliable fixing of the two loop parts 1*a*, 1*b* to one another. The clip 6 can simultaneously provide a clamping effect for firmly clamping the retrieval net 2 by way of the pouch periphery thereof in the net receptacle gap 3 between the two loop parts 1*a*, 1*b*. On account thereof, other connecting/fixing means for holding the two loop parts 1*a*, 1*b* onto one another and/or for firmly holding the retrieval net 2 in the net receptacle gap 3 can optionally be dispensed with.

Figure 8:
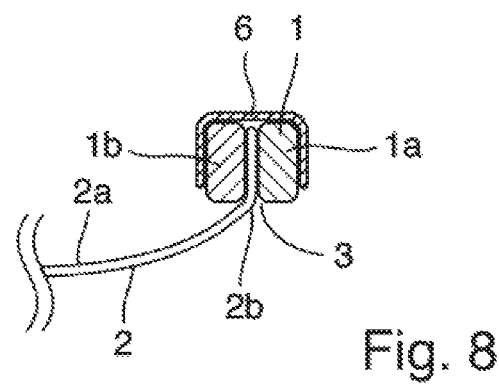
FIG. 8 shows the sectional view of FIG. 5 for a further variant of an embodiment of the present invention having an additional clip.

FIG. 8 shows a modification of the variant of embodiment of FIG. 7 in terms of the clip 6. In the case of this modified variant of embodiment, the clip 6, which in the cross section is U-shaped, at the free ends thereof terminates in a rectilinear manner, that is to say the inward-pointing clip ends 6*a* of the embodiment of FIG. 7 are absent. Accordingly, the loop parts 1*a*, 1*b* in the variant of embodiment of FIG. 8 are not engaged from behind by the clip 6. Nevertheless, depending on the requirement and the specific application, the clip 6 of FIG. 8 can also provide an adequate clamping force for holding together the two loop parts 1*a*, 1*b*, and/or for holding the retrieval net 2 in a firmly clamped manner in the net receptacle gap 3 between the two loop parts 1*a*, 1*b*. When required, the clip 6 can be assisted by additional fixing means for mutually fixing the two loop parts 1*a*, 1*b*, onto one another and/or the retrieval net 2 to the first loop part 1*a* and/or to the second loop part 1*b*.

Figure 9:
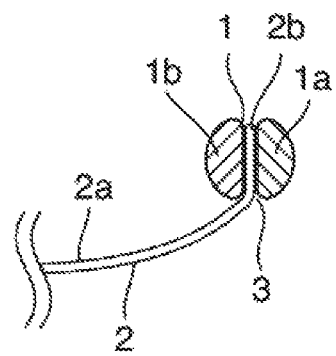
FIG. 9 shows the sectional view of FIG. 5 for a variant of an embodiment of the present invention having loop parts of another cross section.

FIG. 9 shows a variant of embodiment of the instrument of FIGS. 1 to 5, the single difference being that here the two loop parts 1*a*, 1*b* each have an approximately semi-oval cross-section having one substantially planar and one substantially arcuate side. The two loop parts 1*a*, 1*b* by way of the planar sides thereof herein face one another in order for the net receptacle gap 3 lying there between to be formed. This variant of embodiment results in a rather circular cross section for the loop 1 that is formed from the two loop parts 1*a*, 1*b*, while the loop 1 in the exemplary embodiment of FIGS. 1 to 5 has a rather rectangular cross section.

Figure 10:
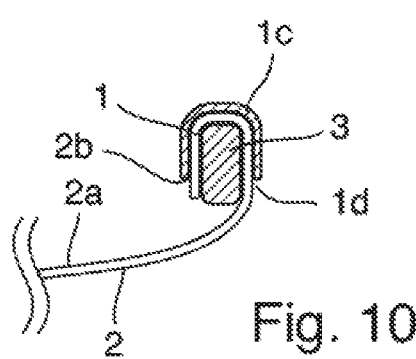
FIG. 10 shows the sectional view of FIG. 5 for a variant of an embodiment of the present invention having loop parts that lie axially inside one another.

FIG. 10 as a further embodiment of the invention shows a medical net-and-loop-type retrieval instrument as a variant of the instrument of FIGS. 1 to 5, the difference being that the loop 1 is formed from a first loop part 1*c* and a second loop part 1*d*, both of which do not have an identical, for example rectangular, cross section, but of which only the second loop part 1*d* has a substantially rectangular cross section, while the first loop part 1*c* has a U-shaped cross section and in a corresponding manner encompasses, or engages across, respectively, the second loop part 1*d* in a U-shaped manner on three sides. On account thereof, the net receptacle gap 3 between the two loop parts 1*c*, 1*d* in the case of this embodiment is correspondingly U-shaped in the cross section. The retrieval net 2 is firmly held in said U-shaped net receptacle gap 3, again in that said retrieval net 2 by way of the free open pouch periphery thereof as the net holding portion 2*b* of the pouch 2*a* that forms the retrieval net 2 is received in the net receptacle gap 3. Here, the pouch periphery lies in the net receptacle gap 3 across the full length of the U-shaped cross section of the latter, such that the pouch periphery is firmly held between the two loop parts 1*c*, 1*d* on three sides of the latter in the net receptacle gap 3. In the case of a given firm clamping force between the two loop parts 1*c*, 1*d*, this enables a very high retention force for the retrieval net 2 on the loop 1. When required, this can be further assisted by a clip-type embodiment of the first loop part 1*c*, to which end the latter by way of the two U-sides thereof is placed in a clamping manner onto the second loop part 1*d*. Prior thereto, the woven-fabric net pouch 2*a* of the retrieval net 2, by way of the pouch periphery of the former, is placed in a U-shaped manner about the second loop part 1*d* such that said woven-fabric net pouch 2*a* is held so as to be firmly clamped in the net receptacle gap 3 when the first loop part 1*c* is placed thereon. Depending on the requirement and the specific application, further fixing means for establishing the retrieval net 2 on the loop 1, or for mutually fixing the two loop parts 1*c*, 1*d*, respectively, can then be dispensed with or be additionally provided.

FIGS. 11 to 16 show a further embodiment of a medical net-and-loop-type retrieval instrument according to the invention, wherein the retrieval net 2 here is formed by a folded-together woven-fabric net hose piece 2*c*. The hose piece 2*c* in the example shown is circumferentially closed and at both end sides is prefabricated or prepared, respectively, so as to be open, as can be seen from FIG. 11. The same components as for the above exemplary embodiment of FIGS. 1 to 5, or for the above embodiment of FIG. 10, can otherwise be used for the instrument of FIGS. 11 to 16, such that reference to this extent can also be made to the above description of said net-and-loop-type retrieval instrument. This applies in particular to the formation of the loop 1 from the first loop part 1*a* or 1*c*, respectively, and the second loop part 1*b* or 1*d*, respectively.

Figure 11:
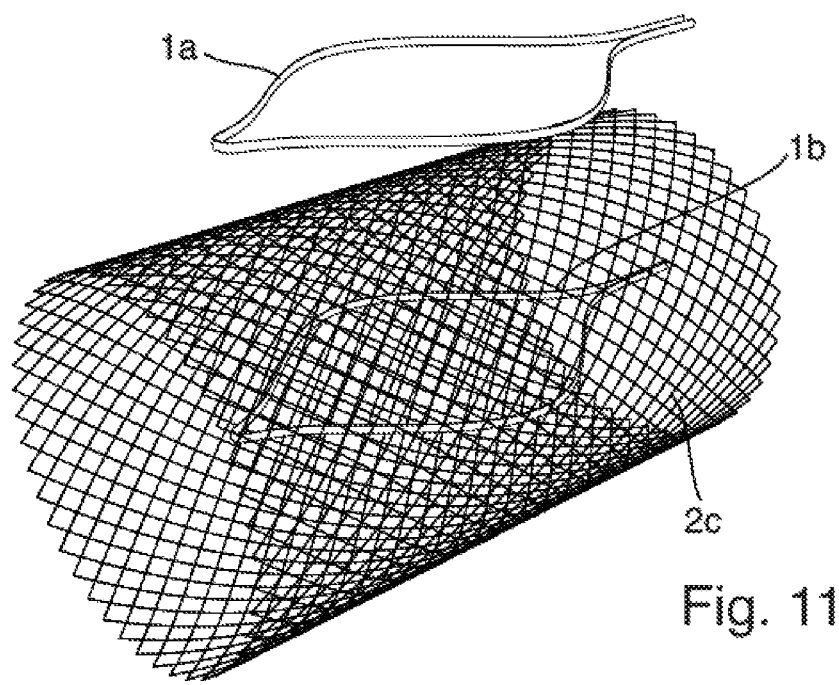
FIG. 11 shows a perspective view of a distal end region of a further an embodiment of a net-and-loop retrieval net instrument of the present invention in an early production stage, having a woven-fabric hose piece that is open at the end side as a retrieval net, and having a loop from an external and an internal loop part.
Figure 12:
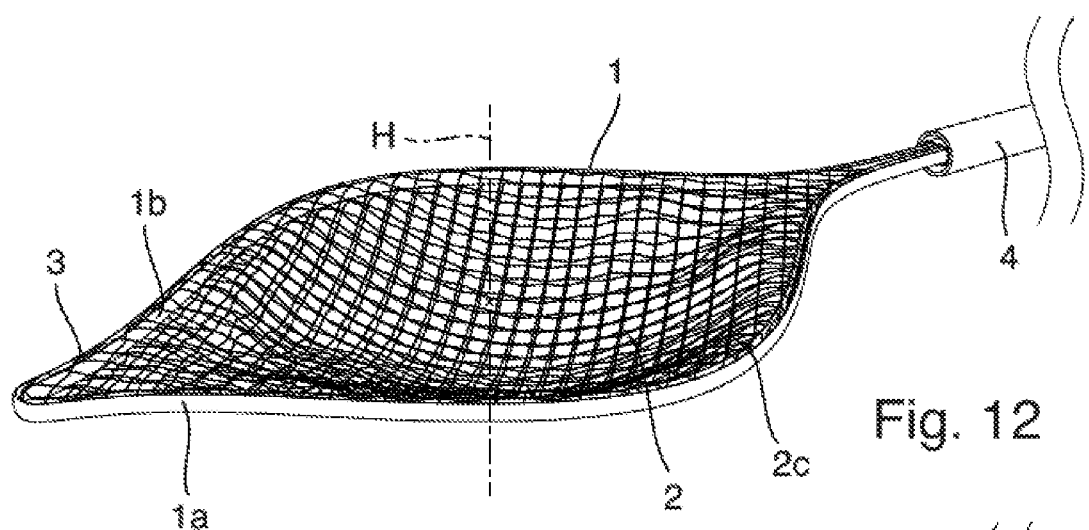
FIG. 12 shows the view of FIG. 1 for the completed instrument of FIG. 11.
Figure 13:
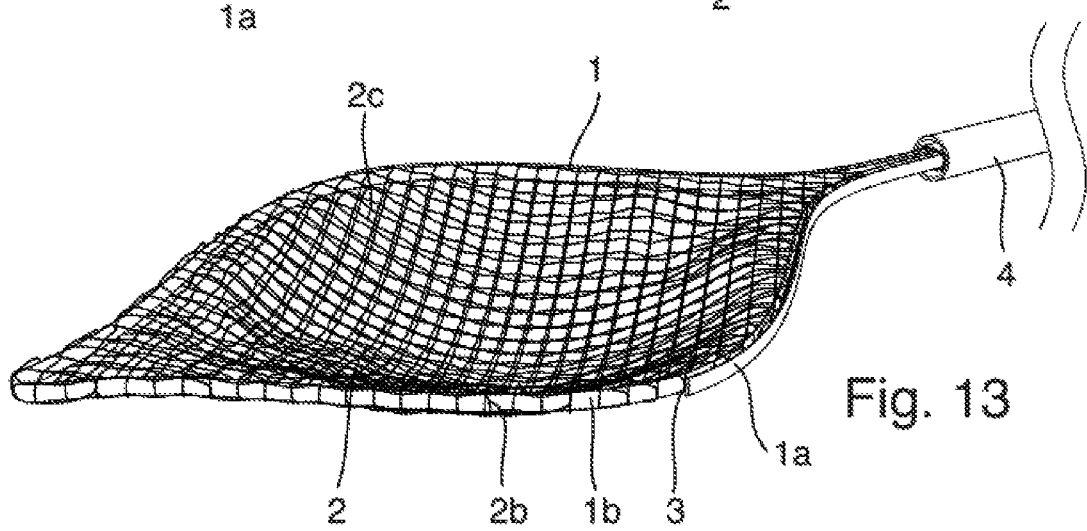
FIG. 13 shows the view of FIG. 2 for the completed instrument of FIG. 11.
Figure 14:
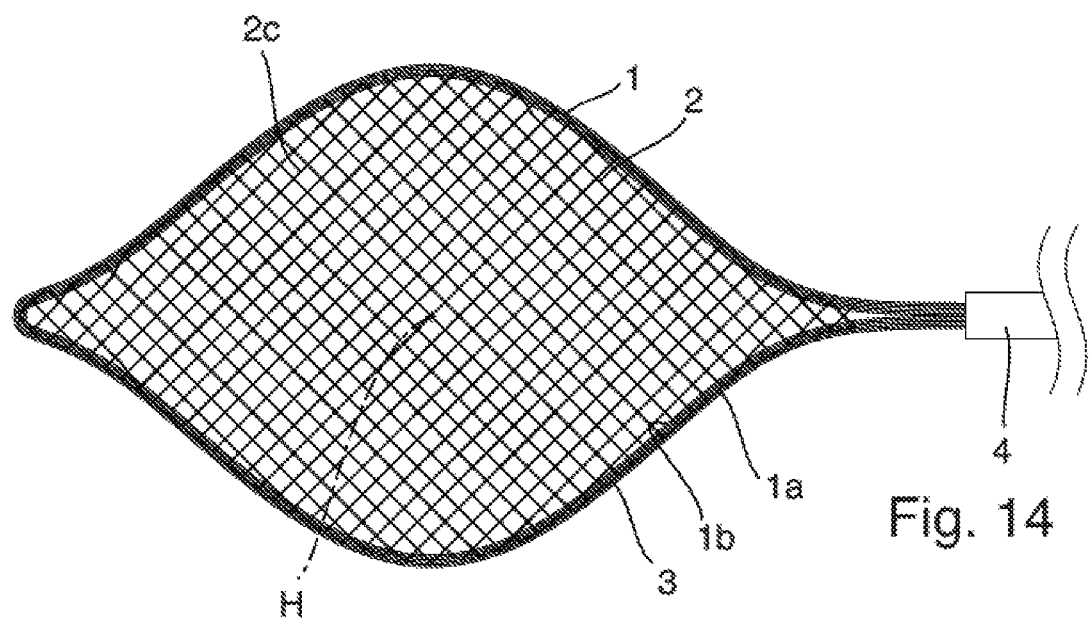
FIG. 14 shows the view of FIG. 3 for the completed instrument of FIG. 11.
Figure 15:
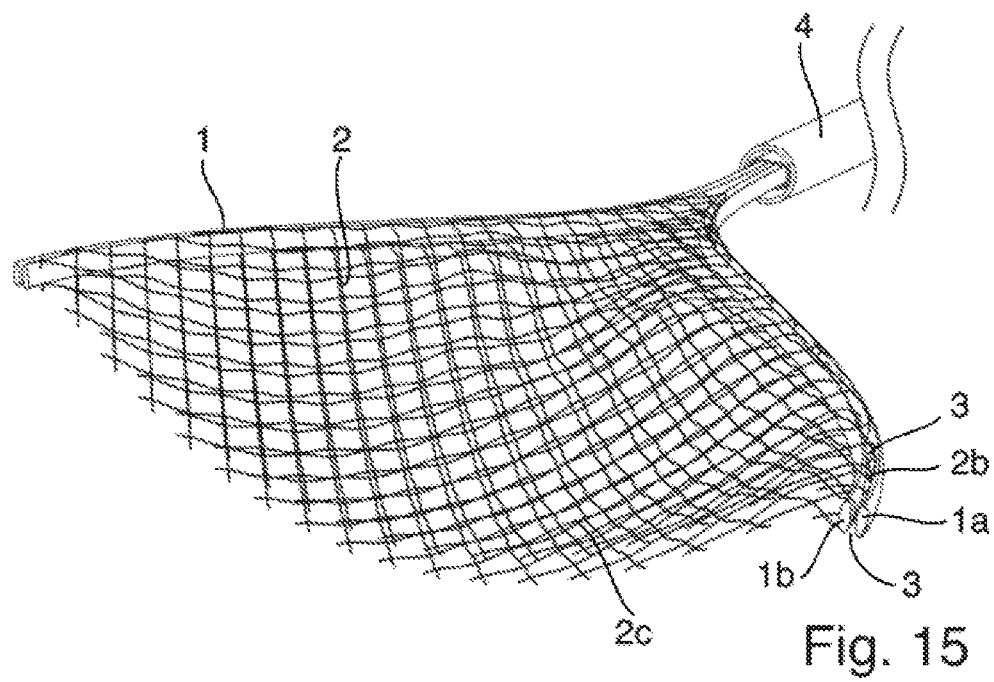
FIG. 15 shows the view of FIG. 4 for the completed instrument of FIG. 11.
Figure 16:
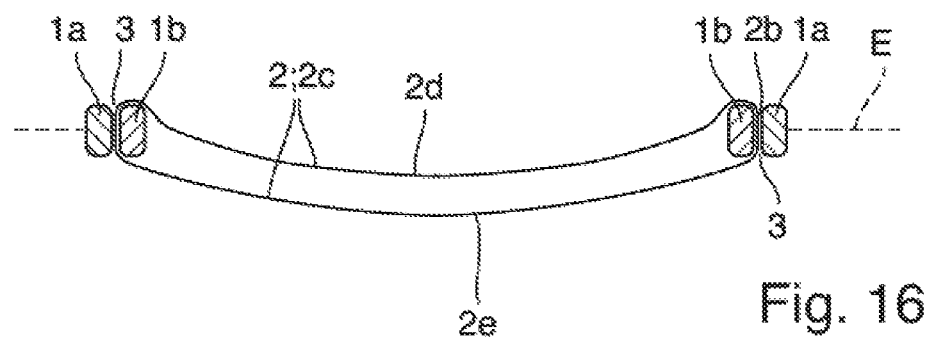
FIG. 16 shows the sectional view of FIG. 6 for the completed instrument of FIG. 11.

For producing the finished loop 1 having the retrieval net 2 in the case of this variant of embodiment, for example when the loop parts 1*a* and 1*b* of the exemplary embodiment of FIGS. 1 to 5 are used, the second inner loop part 1*b* is placed into the interior of the woven-fabric net hose piece 2*c*, as can be seen from FIG. 11, specifically proceeding from one of the two open end sides of the hose piece 2*c*. The hose piece 2*c*, by folding together in a corresponding manner, is then brought to bear on the second loop part 1*b* and from one side pushed through the second loop part 1*b* in order for a desired net bag to be formed. As is likewise visualized in FIG. 11, the outer loop part 1*a* is subsequently placed onto or about, respectively, the inner loop part 1*b* until the outer loop part 1*a* assumes the coaxial position thereof surrounding the inner loop part 1*b*, as can be seen from FIGS. 12 to 16. Prior to or after said attaching of the outer loop part 1*a*, the woven-fabric net hose piece 2*c* that is placed against the inner loop part 1*b* can be closed at the open end sides of said woven-fabric net hose piece 2*c*, when required.

FIGS. 12 to 16, in a manner corresponding to FIGS. 1 to 5, show the instrument completed in such a manner in the distal region thereof that is of interest here. As can be seen from FIGS. 12 to 16, the retrieval net 2, on account of the use of the woven-fabric net hose piece 2*c*, is created in the shape of a double-walled bag or pouch, respectively, having in FIGS. 12 to 16 an upper woven-fabric net tier 2*d* and a lower woven-fabric net tier 2*e*. Since the retrieval net 2 surrounds the inner loop part 1*b* in a circumferentially closed shape, as can be seen in particular from FIG. 16, the retrieval net 2 in the case of this embodiment is already held solely by the inner loop part 1*b*. The outer loop part 1*a*, which bears from the outside in a coaxial manner on the inner loop part 1*b*, fixes the retrieval net 2 so as to be firmly held in this position, in that said outer loop part 1*a* with the inner loop part 1*b* again forms the net receptacle gap 3 lying there between, in which gap the retrieval net 2 is firmly held by way of the net holding portion 2*b* thereof that is situated in said net receptacle gap 3.

In terms of potential mutual fixings of the two loop parts 1*a*, 1*b* and optionally of the retrieval net 2 to one or both loop parts 1*a*, 1*b*, the same implementation variants are possible for the instrument of FIGS. 11 to 16 as have been explained above in the context of the instruments of FIGS. 1 to 10, to which reference may be made. As has been explained, the instrument of FIGS. 11 to 16 can be produced in a comparatively simple manner and, without any additional complexity, enables the retrieval net 2 to be provided in a double-walled embodiment and with a very secure mounting on the loop 1.

As an alternative to the embodiments of FIGS. 1 to 16 having a two-part or multiple-part loop construction, respectively, FIGS. 17 to 22 show embodiments of a single-component or multiple-component integral loop construction.

In the case of the embodiment of FIG. 17, the loop 1 is made as a single-component plastics material injection molded component, the cross section of the retrieval net 2 by way of the net holding portion 2*b* being molded therein. The loop 1 in this case is composed of two loop halves 1*e*, 1*f*, which are mutually opposite in relation to the insert-molded retrieval net 2, wherein the loop half 1*e* can correspond to the outer loop part 1*a* and the loop half 1*f* can correspond to the inner loop part 1*b* of the exemplary embodiment of FIGS. 1 to 5, for example. The retrieval net 2 can again be formed in the shape of a pouch or bag, respectively, in the manner of the woven-net pouch 2*a* of the embodiment of FIGS. 1 to 5, for example. On account of the net holding portion 2*b*, or the pouch periphery, respectively, of said retrieval net 2 being insert-molded in the interior of the cross section of the loop 1, said cross section here being shown to be oval, for example, the retrieval net 2 is securely held on the loop 1 without any further fixing measures.

The production of this variant of instrument in the plastics material injection molding technology can be performed, for example, in such a manner that a retrieval net precursor 2*f* is first incorporated in an injection mold 7, which, in the usual manner, by means of two mold halves 7*a*, 7*b* provides a mold cavity 7*c* as is schematically visualized in FIG. 18. As is schematically visualized in FIG. 19, the plastics material for the loop 1 is subsequently injected into the mold cavity 7*c*, on account of which the net holding portion 2*b* of the retrieval net 2 situated in said mold cavity 7*c* is embedded in the cross section of the molded loop 1. A projecting part of the retrieval net can be cut off, preferably so as to be flush with the surface of the single-component molded loop 1 after the molded loop 1 having the molded-in retrieval net 2 has been retrieved from the mold 7.

FIG. 20, as a further variant of embodiment of the invention, shows an instrument having a two-component integral molded loop construction. In the case of this construction, the loop 1 is composed of a first loop component 1*g* and of a second loop component 1*h* which, in the plastics material injection molding technology, is molded to said first loop component 1*g*, for example. The first loop component 1*g* in the example shown possesses a rectangular cross section, while the remaining cross section of the loop 1 that, as is the case in the exemplary embodiment of FIG. 17, in the cross section is oval is formed from the plastics material of the second loop component 1*h* molded thereon. The retrieval net 2 by way of the net holding portion 2*b* is again situated so as to be approximately centric in the interior of the cross section of the loop 1, to the extent of one part between the two loop components 1*g*, 1*h* and to the extent of the remaining part in the interior of the second loop component 1*h* that is injected-molded on both sides. As is the case in the exemplary embodiment of FIG. 17, one side of the cross section of the loop 1 on the one or the other side of the retrieval net 2, respectively, or of the net holding portion 2*b* of the latter, respectively, can in each case correspond to their radially outer loop part 1*a*, or to the radially inner loop part 1*b*, respectively, of the embodiment of FIGS. 1 to 5. The first loop component 1*g* can, for example, be composed of a super elastic metal material such as a nickel/titanium alloy. In order for the instrument to be produced, the first loop component 1*g*, conjointly with the net holding portion 2*b* of the retrieval net 2, can be placed in a plastics material injection mold corresponding to the mold 7 of FIG. 18, whereupon the plastics material for the second loop component 1*h* is injection-molded thereto.

FIG. 21 shows a variant of embodiment of the invention which corresponds to that of FIG. 20, having the modification that not a net pouch as in the example of FIGS. 1 to 5 but the hose piece 2*c* corresponding to the exemplary embodiment of FIGS. 11 to 16 is used as the initial product for the retrieval net 2. For the production, in this case, the hose piece 2*c* by way of a circumferential portion as the net holding portion 2*b* can be placed in a plastics injection mold corresponding to the mold 7 of FIG. 18, for example conjointly with the first loop component 1*g*. In an alternative embodiment having a single-component integral loop construction, as is the case in the embodiment of FIGS. 17 to 19, only the hose piece 2*c* is placed in the mold cavity and is overmolded with a material of the then single-component loop 1 in the net holding portion 2*b*.

FIG. 22 shows a further variant of embodiment as a modification of the exemplary embodiment of FIG. 21. The loop in the case of the variant of embodiment of FIG. 22 having a two-component integral loop construction is composed of a loop core as the first loop component 1*g* and of a sheathing as the second loop component 1*h* from a plastics material which in the cross section completely surrounds the core-forming first loop component 1*g*, that is to say that the material of the core-forming first loop component 1*g* in this case is overcast by material of the sheath-forming second loop component 1h, i.e. insert-cast in the latter. The net holding portion 2b of the retrieval net 2 that again is configured in two tiers from the hose piece 2c, having the net tiers 2d and 2e, is situated between the two loop components 1g, 1h. The net holding portion 2b in the example shown here completely circumferentially loops about the core-forming loop component 1g such that both net tiers 2d, 2e so as to bear on one another are guided out of the loop 1 on an identical side, in the cross sectional view of FIG. 22 on the lower narrow side of the loop 1. In the case of this variant of embodiment, the loop 1 thus circumferentially remains completely free of the retrieval net 2, with the exception of the exit location of the retrieval let 2 on the narrow side of the loop, and to this extent can have a completely smooth surface profile corresponding to the cast sheath-forming loop component 1h, for example. On account of the enclosure of the core-forming loop component 1g and the overcasting by the material of the sheath-forming loop component 1h, the retrieval net 2 is very reliably held on the loop 1 without any other fixing measures being required.

Figure 23:
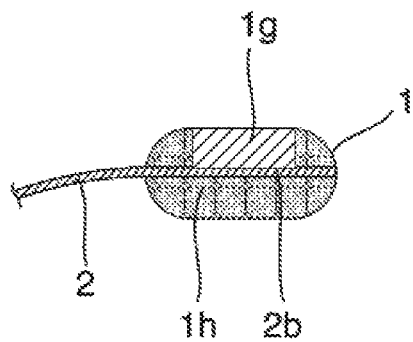
FIG. 23 shows the sectional view of FIG. 20 for a variant of an embodiment of the present invention having a loop assembly rotated by 90°.

In the embodiments of FIGS. 1 to 20, the retrieval net is in each case inserted into the loop so as to be perpendicular to the loop plane, for example on a lower side of the loop. In alternative embodiments such as shown in the embodiment of FIG. 23, the retrieval net 2 is inserted into the loop 1 so as to be parallel with the loop plane. FIG. 23 shows this by way of an example of a two-component loop embodiment corresponding to FIG. 20; in alternative embodiments, the loop is embodied as having a single component or in multiple parts, in a manner analogous to the exemplary embodiments of FIGS. 1 to 19. In the case of these variants of embodiment having a retrieval net that is inserted so as to be parallel with the loop plane, the cross section of the loop 1, as in the case of FIG. 23, preferably has a length which in the loop plane is larger than in the plane perpendicular to the latter, as opposed to the variants according to FIGS. 17 and 20, for example.

Figure 24:
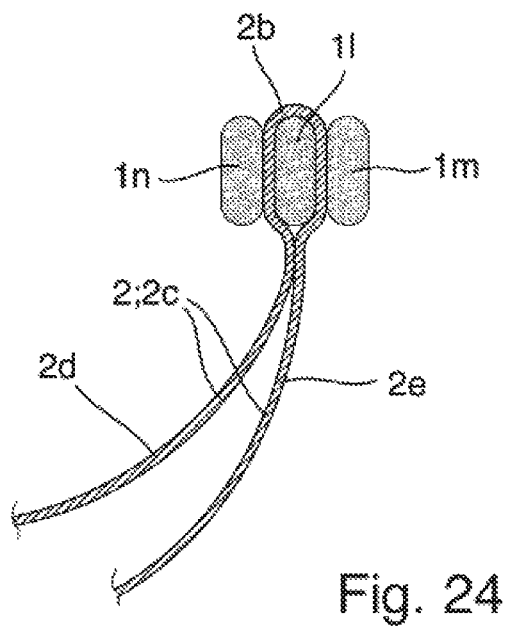
FIG. 24 shows a sectional view of FIG. 5 for a variant of an embodiment of the present invention having a woven-fabric hose piece for the retrieval net and a three-part loop.

FIG. 24 visualizes a variant of embodiment of the invention having three conforming loop parts, a central loop part 1l, an outer loop part 1m, and an inner loop part 1n. The retrieval net 2 in this example is formed in two tiers, in a manner analogous to the variant of embodiment of FIG. 22, having the net tiers 2d and 2e from the hose piece 2c, wherein the net holding portion 2b loops about the central loop part 1l, such that both net tiers 2d, 2e are again guided out of the loop 1 on an identical side, preferably on the lower side of the loop from which the retrieval net, proceeding from the loop plane, extends downward. The net holding portion 2b herein is held between the central loop part 1l and the outer loop part 1m, on the one hand, and between the central loop part 1l and the inner loop part 1n, on the other hand. The fixing of the three loop parts 1l, 1m, 1n and of the net holding portion 2b of the retrieval net 2 can be performed in a manner explained above in the context of the other embodiments, for example by mutually fixing all four parts or by fixing the net holding portion 2b to one, two, or all three, loop parts 1l, 1m, 1n, and/or by fixing the three loop parts 1l, 1m, 1n in each case in pairs or collectively.

As is highlighted by the embodiments shown and explained above, the invention makes available a medical net-and-loop retrieval instrument which can be produced in a comparatively simple manner and offers a very high reliability in terms of function and fail-safe performance. In particular, the retrieval net is held very reliably and secured against undesirable displacements on the loop by way of a relatively minor complexity.

It is understood that the invention comprises further advantageous embodiments, for example such in which the loop is integrally constructed from three, four, or more conforming loop parts that bear on one another, or from three, four, or more loop components in a conventional metal or plastics material casting technology, wherein the net receptacle gap is formed between at least two of said loop parts or loop components, respectively. Besides the pouch shape/bag shape shown, arbitrary other retrieval net shapes which are known per se for this intended application can be used for the retrieval net.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A medical net-and-loop type retrieval instrument, comprising:
   a distal loop; and
   a retrieval net that by way of a net holding portion is held on the loop,
   wherein
   the retrieval net by way of the net holding portion is firmly held by the loop in an interior of a cross section of the loop,
   the loop includes at least two conforming loop parts which, while leaving a net receptacle gap therebetween, are connected so as to bear on one another,
   the retrieval net by way of the net holding portion is firmly held in the net receptacle gap, and
   wherein
   at least a first and a second of the loop parts are fixed to one another by at least one clamped joint connection or at least one adhesively bonded joint connection or at least one welded/soldered joint connection or a first one of the loop parts has a U-shaped cross section and a second one of the loop parts has a rectangular cross section, the first one of the loop parts encompassing the second one of the loop parts on three sides.

2. The medical net-and-loop type retrieval instrument as claimed in claim 1, further comprising:
   a clip which at least in portions encompasses at least the first and the second loop part so as to conjointly clamp said first and second loop part.

3. The medical net-and-loop type retrieval instrument as claimed in claim 1, wherein
   the loop includes an outer and an inner loop part, and
   the outer loop part surrounds the inner loop part and, by way of an internal circumference, faces an external circumference of the inner loop part.

4. The medical net-and-loop type retrieval instrument as claimed in claim 1, wherein the loop is integrally formed with the net holding portion of the retrieval net embedded in the interior of the cross section of the loop.

5. The medical net-and-loop type retrieval instrument as claimed in claim 1, wherein the retrieval net is held on the loop by at least one clamped joint connection or at least one adhesively bonded joint connection or at least one welded/soldered joint connection.

6. The medical net-and-loop type retrieval instrument as claimed in claim 1, wherein the retrieval net is formed by a woven-fabric net pouch which by way of a pouch periphery is firmly held on the loop.

7. The medical net-and-loop type retrieval instrument as claimed in claim 1, wherein
   at least a first one of the loop parts, by means of an adhesively bonded joint connection, is connected to at least one of the net holding portion of the retrieval net and at least a second one of the loop parts,
   said adhesively bonded joint connection is situated exclusively on an upper side of the loop, and
   the retrieval net extends into the loop only on an opposite lower side.

8. A medical net-and-loop type retrieval instrument, comprising:
   a distal loop; and
   a retrieval net that by way of a net holding portion is held on the loop,
   wherein
   the retrieval net by way of the net holding portion is firmly held by the loop in an interior of a cross section of the loop,
   the loop is integrally formed with the net holding portion of the retrieval net embedded in the interior of the cross section of the loop,
   the loop is a multi-component casting having at least one first loop component from a first material of metal or plastics material and a second loop component molded to said first loop component,
   the second loop component is formed from a second material that is different from the first material, and
   the retrieval net at the net holding portion thereof is held so as to be cast between the loop components.

9. The medical net-and-loop type retrieval instrument as claimed in claim 8, wherein the retrieval net is held on the loop by at least one clamped joint connection or at least one adhesively bonded joint connection or at least one welded/soldered joint connection.

10. The medical net-and-loop type retrieval instrument as claimed in claim 8, wherein the retrieval net is formed by a woven-fabric net pouch which by way of a pouch periphery is firmly held on the loop.

11. A medical net-and-loop type retrieval instrument, comprising:
    a distal loop; and
    a retrieval net that by way of a net holding portion is held on the loop,
    wherein
    the retrieval net by way of the net holding portion is firmly held by the loop in an interior of a cross section of the loop, and
    the retrieval net is formed by a folded-together woven-fabric net hose piece which is circumferentially closed and which in a circumferential direction extends through the interior of the cross section of the loop.

12. The medical net-and-loop type retrieval instrument as claimed in claim 11, wherein the retrieval net is held on the loop by at least one clamped joint connection or at least one adhesively bonded joint connection or at least one welded/soldered joint connection.

13. The medical net-and-loop type retrieval instrument as claimed in claim 11, wherein the retrieval net is formed by a woven-fabric net pouch which by way of a pouch periphery is firmly held on the loop.

* * * * *